US 9,192,737 B2

(12) United States Patent
El-Shammaa et al.

(10) Patent No.: US 9,192,737 B2
(45) Date of Patent: *Nov. 24, 2015

(54) ADJUSTING A POSITION OF A HEATING WIRE WITHIN A BREATHING CIRCUIT

(71) Applicant: CareFusion 207, Inc., San Diego, CA (US)

(72) Inventors: Michael El-Shammaa, Anaheim, CA (US); Chris Zollinger, Chino Hills, CA (US)

(73) Assignee: CAREFUSION 207, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/719,458

(22) Filed: May 22, 2015

(65) Prior Publication Data

US 2015/0250975 A1 Sep. 10, 2015

Related U.S. Application Data

(63) Continuation of application No. 12/879,944, filed on Sep. 10, 2010, now Pat. No. 9,067,037.

(51) Int. Cl.
*B23P 11/00* (2006.01)
*A61M 16/10* (2006.01)
*A61M 16/08* (2006.01)

(52) U.S. Cl.
CPC ....... *A61M 16/1075* (2013.01); *A61M 16/1095* (2014.02); *A61M 16/0816* (2013.01); *A61M 2209/00* (2013.01); *Y10T 29/49826* (2015.01); *Y10T 29/53* (2015.01)

(58) Field of Classification Search
CPC .............. A61M 16/1095; A61M 16/1075; A61M 16/0816; A61M 2209/00; Y10T 29/49826; Y10T 29/53

USPC ................ 254/134.3 FT, 134.4; 128/204.17, 128/204.18

See application file for complete search history.

(56) References Cited

U.S. PATENT DOCUMENTS

| 549,757 A | 11/1895 | Volland |
| 4,967,744 A | 11/1990 | Chua |
| 5,392,770 A | 2/1995 | Clawson et al. |

(Continued)

FOREIGN PATENT DOCUMENTS

| WO | 9718001 | 5/1997 |
| WO | 2004105847 | 12/2004 |

OTHER PUBLICATIONS

International Search Report and Written Opinion for PCT/US2011/047303 issued on Mar. 19, 2012 (10 pages).

(Continued)

*Primary Examiner* — David Bryant
*Assistant Examiner* — Steven A Maynard
(74) *Attorney, Agent, or Firm* — McDermott Will & Emery

(57) ABSTRACT

A wire adjuster for adjusting a position of an element within a limb of a breathing circuit is described. The wire adjuster includes an interior wall engaging portion configured for engaging a surrounding interior wall of said limb and an element receiving portion coupled with the interior wall engaging portion, wherein the element receiving portion is configured for releasably securing the element as the wire adjuster is movably engaging with the surrounding interior wall, such that the wire adjuster can be used to selectively locate an element within the limb of the breathing circuit.

20 Claims, 6 Drawing Sheets

(56) References Cited

U.S. PATENT DOCUMENTS

| | | |
|---|---|---|
| 5,423,860 A | 6/1995 | Lizardi et al. |
| 5,701,887 A * | 12/1997 | Rustad et al. ............ 128/204.17 |
| 5,823,184 A | 10/1998 | Gross |
| 6,874,500 B2 | 4/2005 | Fukunaga et al. |
| 7,178,521 B2 | 2/2007 | Burrow et al. |
| 2004/0250815 A1 * | 12/2004 | Scott et al. ............... 128/204.17 |

OTHER PUBLICATIONS

International Search Report and Written Opinion for PCT/US2011/047921 issued on Mar. 27, 2012 (10 pages).

* cited by examiner

ADJUSTING A POSITION OF A HEATING WIRE WITHIN A BREATHING CIRCUIT

CROSS-REFERENCE TO RELATED APPLICATIONS

This application is a continuation of U.S. patent application Ser. No. 12/879,944 filed on Sep. 10, 2010, now U.S. Pat. No. 9,067,037, the entire content of which is hereby incorporated by reference herein.

FIELD OF THE INVENTION

The present technology relates generally to the respiratory field. More particularly, the present technology relates to a breathing circuit.

BACKGROUND

In general, a breathing circuit is an assembly of components which connects a patient's airway to a machine creating an artificial atmosphere, from and into which the patient breaths. For example, the machine may be a ventilator and the components may be a series of tubes. When the ventilator pushes air through a tube to a patient, the air is heated by a heating wire positioned within the tube. Different types of breathing circuits accommodate different flow rates of air. Sometimes during treatment, a caregiver needs to alter the breathing circuit to accommodate a different flow rate of air for the patient. In this situation, the caregiver replaces the breathing circuit being used with a different breathing circuit. This is a very costly procedure for a hospital because the hospital must stock a variety of breathing circuits for different patient needs.

Figure 1:
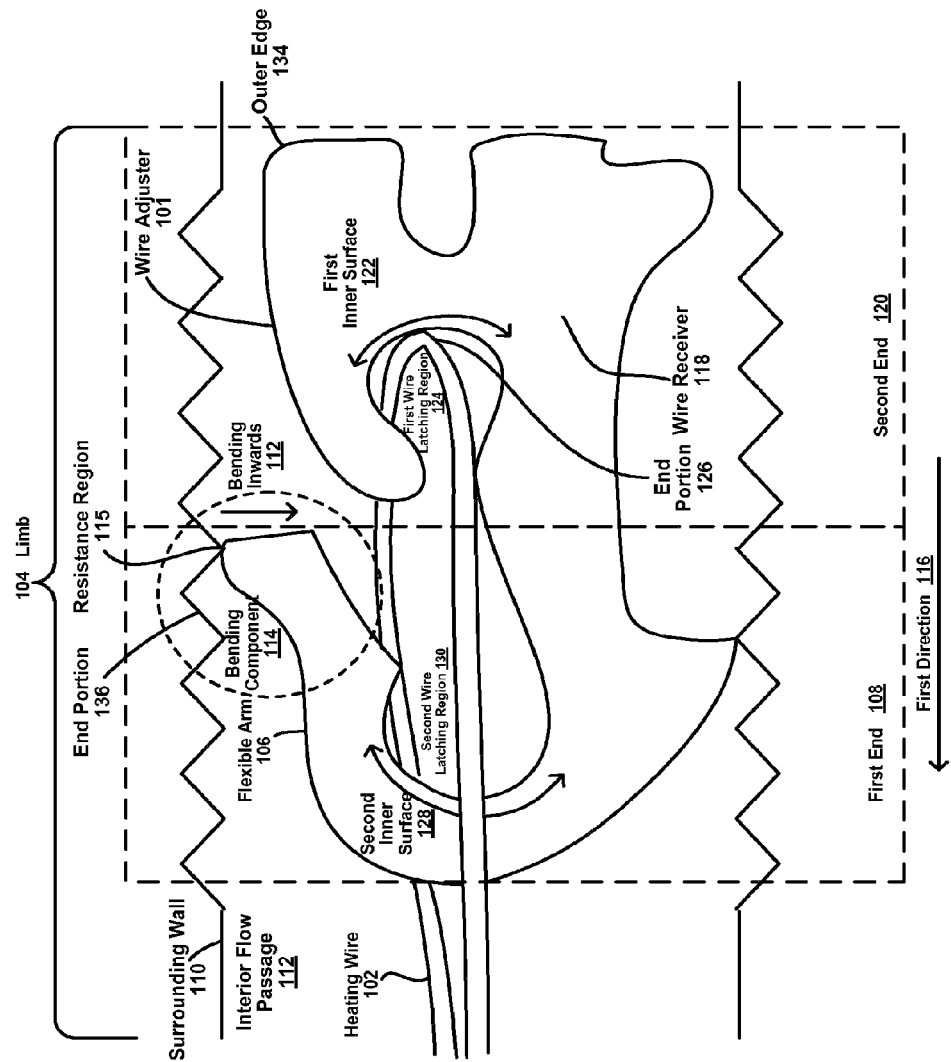
FIG. 1 is a perspective view of a wire adjuster within a limb in a bending position, according to one embodiment of the present technology.

The drawings referred to in this description should not be understood as being drawn to scale unless specifically noted.

DETAILED DESCRIPTION OF THE PREFERRED EMBODIMENTS

The discussion will begin with an overview of the general use of breathing circuits and the limitations associated therewith. The discussion will then focus on embodiments of the present technology that provide a wire adjuster for adjusting a position of a heating wire within a limb of a breathing circuit.

Overview

Breathing circuits are utilized to deliver such medical support as air and anesthetics from a machine that creates an artificial environment to a patient via tubes. Breathing circuits are used in surgical procedures. For example, in a most general case, breathing circuits comprise an inspiratory limb running from a ventilator to a patient and an expiratory limb running from the patient back to the ventilator. The ventilator pushes air through the inspiratory limb to reach the patient. The patient inhales this pushed air and exhales air into the expiratory limb.

If the air is cold when the patient inhales it, the patient's body works hard to try to warm up the air for ease of breathing. Thus, breathing circuits are designed with heating wires positioned within the interior of at least the inspiratory limb. If a heating wire is positioned within the inspiratory limb such that the heating wire stretches the full length of the inspiratory limb, then all of the air moving through the inspiratory limb becomes heated. Thus, the air arriving from the inspiratory limb into the patient's mouth is also well heated.

However, if the heating wire is positioned such that it stretches for only two thirds of the way towards the patient's mouth while within the inspiratory limb, then the heated air that travels the final section of the inspiratory limb to the patient's mouth has time to cool off. This is especially true if the flow rate of the air being pushed by the ventilator is low. However, if the air being pushed by the ventilator is moving at a fast rate, then this air retains much of its heat since the cooling off time as the air moves through the unheated sections is relatively minimal.

If the heating wire within the inspiratory limb is positioned too close to the patient's mouth while the air is moving at a fast rate, then the heated air may be too hot and scorch the patient during inhalation. On the other hand, if the heating wire within the inspiratory limb is positioned too far away from the patient's mouth while the air is moving at a slow rate, then the air may be too cool for the patient, thereby causing the patient's body to work harder to heat up the air.

Thus, a variety of breathing circuits exist that provide a desired temperature of heated air to the patient while also applying a desired rate of air flow to the patient. If it is determined that a patient needs a high rate of air flow during treatment, but is currently using a breathing circuit that only accommodates a low rate of air flow, the caregiver must disengage the breathing circuit from the patient and replace it with an appropriate breathing circuit. For example, the caregiver may decide that there is a need to increase the flow rate of air to 5 L/min from 2 L/min. The caregiver would change the breathing circuit to one that has a heating wire that is positioned to be farther from the patient.

Thus, the hospital must stock a variety of breathing circuits to accommodate patients' breathing needs during surgical treatment. More particularly, a hospital may have to stock a large number of different breathing circuits in advance of performing services for the patient. Thus, the current method of exchanging one breathing circuit for another during treatment is costly for the caregiver.

Embodiments of the present technology provide a device for adjusting a position of a heating wire within a breathing circuit to accommodate a different flow rate of air. The device may be pushed from one position to another in a first direction within the limb. In one embodiment, the limb comprises one or more projections and one or more depressions relative to the projections on its interior surface. A flexible arm of the device engages with the projections and depressions by bending inwards or expanding into a more relaxed position as the flexible arm moves over the projections and depressions, respectively.

For example, the flexible arm is pushed inwards by the projection as the flexible arm is pushed by the projection and through the limb. The flexible arm expands into a more relaxed position from its bent position as it moves over depressions while being pushed through the limb.

In a further embodiment of the present technology, while the device is in a more relaxed state than its immediately previous bent position caused by moving over a projection, an outer corner of the flexible arm is held in place by the just circumvented projection. While the device is locked in place by the projection, the projection blocks the device from moving backwards. However, the device may still be pushed through the limb, as it may still bends inward to overcome any further projections positioned along the pathway of the first direction. In one embodiment, the device may be pushed to a predetermined position according to instructions encoded on the limb.

The following discussion will begin with a description of the structure of the components of the present technology. This discussion will then be followed by a description of the components in operation.

Structure

With reference now to 100 of FIG. 1, a perspective view of a wire adjuster 101 within a limb 104 is shown. In this embodiment, a wire adjuster 101 for adjusting a position of a heating wire 102 within a limb 104 of a breathing circuit is shown.

In one embodiment, the wire adjuster 101 comprises a flexible arm 106 configured for engaging a surrounding wall 110 of an interior flow passage 112 of the limb 104 and a wire receiver 118 configured for releasably securing the heating wire as the wire adjuster is movably engaging with the surrounding wall 110. The flexible arm 106 and the wire receiver 118 are coupled with each other. In one embodiment, the flexible arm 106 is positioned at a first end 108 of the wire adjuster 101 and the wire receiver 118 is positioned at a second end 120 of the wire adjuster 101.

Figure 2:
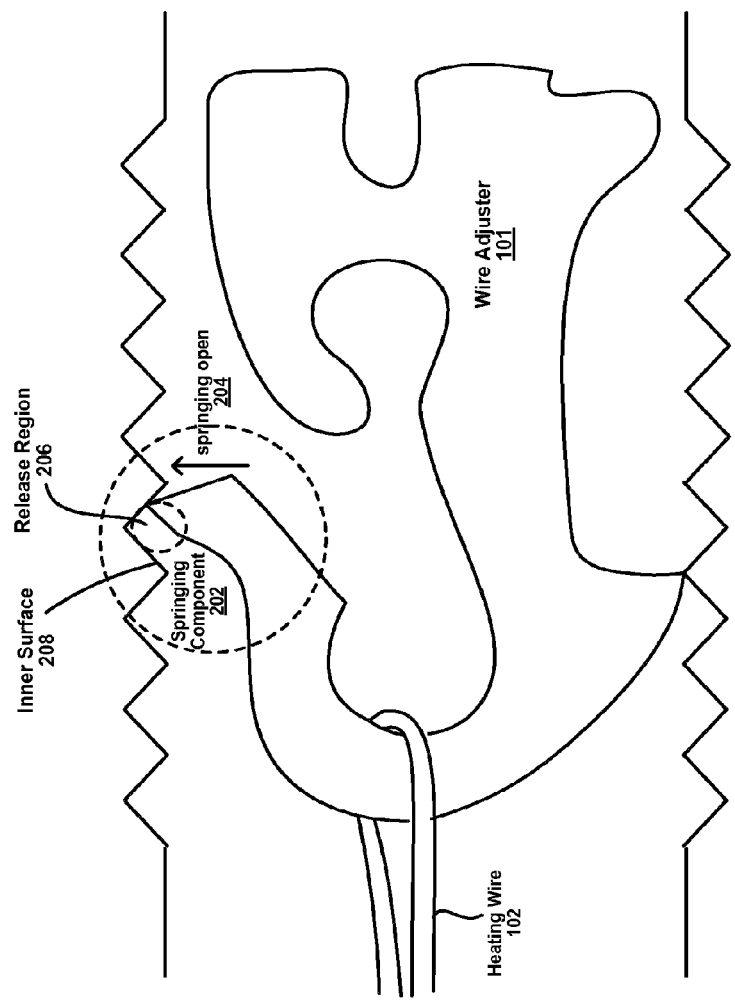
FIG. 2 is a perspective view of a wire adjuster within a limb in a sprung position, according to one embodiment of the present technology.

FIG. 2 is a perspective view of a wire adjuster 101 within a limb 104 in a sprung position, according to one embodiment of the present technology. Thus, with reference to FIG. 1 and to FIG. 2, in one embodiment the flexible arm 106 comprises a bending component 114 and a springing component 202. Of note, the flexible arm 106 may be of any shape that enables bending and the ability to spring back.

In one embodiment, the bending component 114 is configured for movably engaging with the surrounding wall 110 by bending inwards 112 at a resistance region 115 of the surrounding wall 110 as the wire adjuster 101 is pushed through the interior flow passage 112 in a first direction 116. More specifically, while the bending component 114 moves along that interior flow passage 112 in a first direction, it engages with the surrounding wall 110. Engagement with the surrounding wall 110 includes being in contact with portions of the surrounding wall 110.

For example, the bending component 114 makes contact with a resistance region 115, a projection 402 (of FIG. 4) or any resisting points. The resistance region 115 is an area along the limb 104 that includes a ridge, projection, etc. at which the end portion of the flexible arm 106 must bend inwards 112 in order to pass by the passable obstacle. For example, the ridge provides resistance to the flexible arm 106 that is overcome by the adjuster wire 101 being pushed through the limb 104. Due to the flexibility of the bending component 114, the flexible arm 106 bends inwards as it passes over a projection 402.

In one embodiment, the springing component 202 is configured for immovably engaging with the surrounding wall 110 by springing open 204 at a release region 206 of the surrounding wall 110 until a sufficient pushing force is applied to the wire adjuster 101 while being pushed in the first direction 116 through the limb to activate the bending component 114. For example, the springing component 202 engages with the surrounding wall 110, without moving. Thus, the springing component 202 is in contact with the surrounding wall 110.

In this situation, the springing component 202 is resting within a release region 206 of the limb 104. The release region 206 is an area in which there is a depression along the surrounding wall 110 of the interior flow passage 112. The depressions may be a result of a corrugated design, in which there are ridges and troughs. In another embodiment, the depressions may be a result of a design with projections spaced a predetermined distance apart form each other. The depression may actually only be a depression relative to the prior projection. Thus, it should be appreciated that the design of the limb 104 and its interior portions, such as a surrounding wall 110 of an interior flow passage 112, affects the functioning of the wire adjuster 101.

In other words, in one embodiment, an end portion 136 of the flexible arm 106 is configured for immovably engaging with an inner surface of a trough on the surrounding wall 110, wherein a portion of the limb 104 is of a corrugated design. In another embodiment, an end portion 136 of the flexible arm 106 is configured for immovably engaging with a projection 402 (of FIG. 4) on the surrounding wall 110.

Referring still to FIGS. 1 and 2, in one embodiment, the wire receiver 118 comprises a first inner surface 122 defining a first wire latching region 124. The first wire latching region 124 is configured for holding an end portion 126 of the heating wire 102 as the wire adjuster 101 is movably engaging with the surrounding wall 110. In one embodiment, the first inner surface 122 is an inner curvature. In another embodiment, the first inner surface 122 may be a block-shape inner surface 122. In one embodiment, the end portion 126 of the heating wire 102 is looped. In another embodiment, the end portion 126 of the heating wire 102 is hook-shaped.

In yet another embodiment, the first wire latching region 124 is an area of space that is defined by a shape of a hook. It should be appreciated that the first wire latching region 124 may be any shape that accommodates retaining any element that may be pushed through the interior flow passage 112 with the wire adjuster 101, such as a heating wire 102.

Referring still to FIGS. 1 and 2, in one embodiment, the flexible arm 106 comprises a second inner surface 128 defining a second wire latching region 130 that is open to the first wire latching region 124. The second wire latching region 130 is configured for holding the heating wire 102 as the springing component 202 immovably engages with the surrounding wall 110.

For example, as the springing component 202 is sprung open 204 as far as it can go into the release region 206, the springing component 202 is engaging with the surrounding wall 110 through contact. The springing component 202 is also remaining substantially stationary because a sufficient force is not being applied to the wire adjuster 101 to move the wire adjuster 101 (and hence the bending component 114 of the flexible arm 106) over the next immediate resistance region 115 (or projection 402 of FIG. 4). By substantially stationary, it is meant that the springing component 202 may be slightly moving due to a very minimal force being applied in the first direction 116 upon the wire adjuster 101. However and as explained, this force is not enough to cause the bending component 114 to activate and therefore bend inwards 112 in order to pass by the resistance region 115 (or projection 402 of FIG. 4).

In one embodiment, a wire tension component produces a tension in the heating wire 102 such that during the operation of the wire adjuster 101, the heating wire 102 is always being pulled at a minimal force in the first direction 116. Thus, if the springing component 202 is immovably engaging the surrounding wall 110 in the release region 206, the built-in tension in the heating wire 102, being pulled in the first direction 116, will cause the heating wire 102 to spring to a position such that it becomes at least temporarily hooked in the second wire latching region 130.

Figure 3:
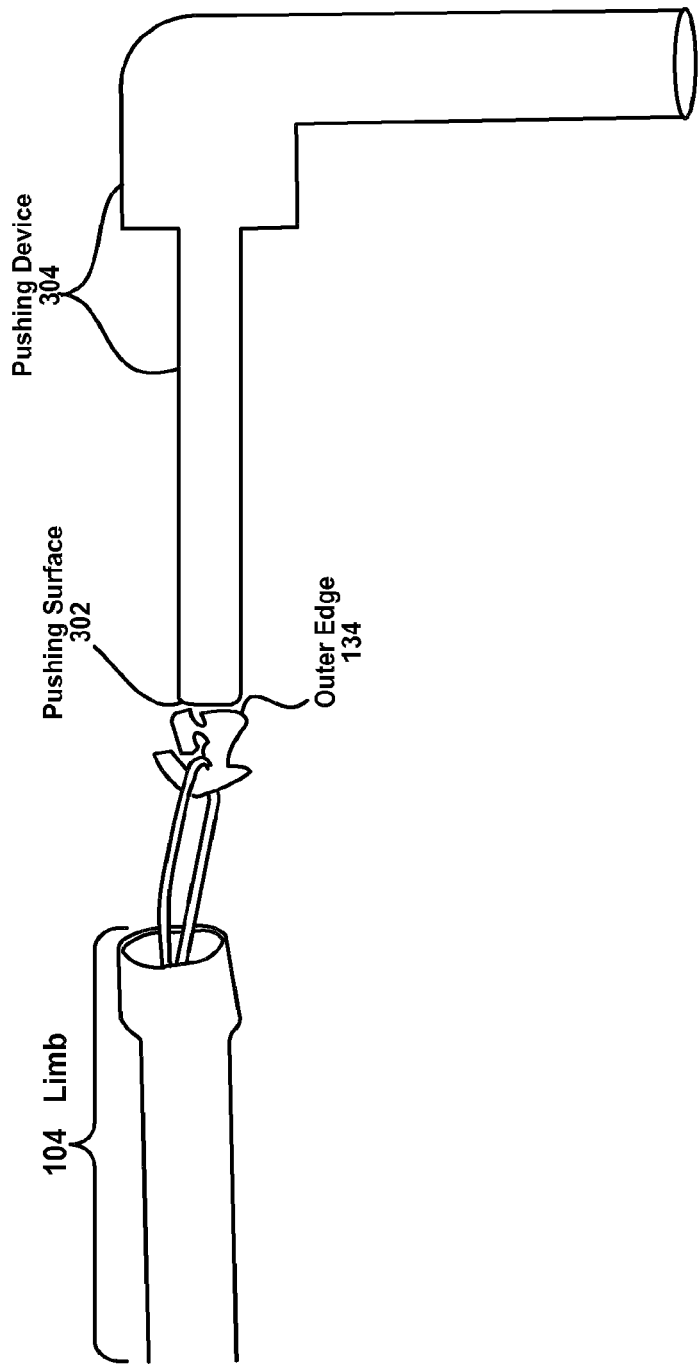
FIG. 3 is a perspective view of a pushing device pushing a wire adjuster, according to one embodiment of the present technology.

FIG. 3 is a perspective view of a pushing device pushing a wire adjuster 101, according to one embodiment of the present technology. Referring now to FIGS. 1-3, in one embodiment, the wire receiver 118 comprises an outer edge 134 configured for being pushed upon by a pushing surface 302 of a pushing device 304 with a force that moves the wire adjuster 101 through the interior flow passage 112. While pushing device 304 is shown in FIG. 3 with a specific outline, it should be appreciated that a pushing device may be any means by which the wire adjuster 101 may be pushed through the interior flow passage 112 of the limb 104.

In one embodiment, and still referring to FIGS. 1-3, the outer edge 134 is flat. While in another embodiment, the outer edge 134 has a grooved surface that is compatible with the pushing surface 302 of the pushing device 304.

Figure 4:
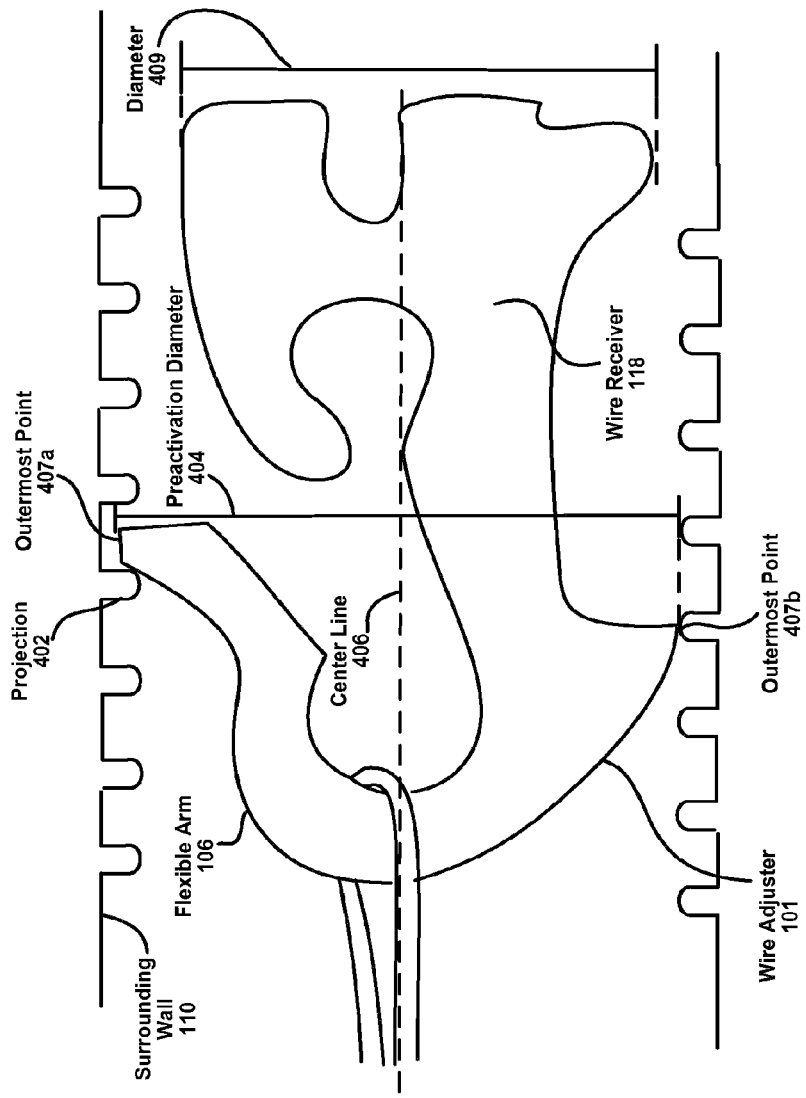
FIG. 4 is a perspective view of a wire adjuster within a limb approaching a projection, according to one embodiment of the present technology.

FIG. 4 is a perspective view of a wire adjuster 101 within a limb 104 that is approaching a projection 402, according to one embodiment of the present technology. Referring now to FIG. 4, in one embodiment, the flexible arm 106 has a pre-activation diameter 404 that is greater than a diameter 409 of the wire receiver 118. The pre-activation diameter 404 is measured from a center line 406 of the wire adjuster 101 to the outer most points 407a and 407b of the flexible arm 106. This design enables the wire adjuster 101 to move through the interior flow passage 112 without the wire receiver 118 interrupting the functioning, as described herein, of the flexible arm 106.

In one embodiment, FIGS. 1 and 2 show a device for movably securing a heating wire 102 within a limb 104, that is an inspiratory limb. In one embodiment, the device is a wire adjuster 101 with a flexible arm component 106 coupled with a wire receiver 118.

In one embodiment, the flexible arm 106 is positioned at a first end 108 of the wire adjuster 101 and configured for unlocking and locking in response to contact with a resistance and a release region, 115 and 206, respectively, on a surrounding wall 110 of an interior flow passage 112 of the inspiratory limb 104.

In one embodiment, the unlocking comprises bending inwards 112 at the resistance region 115 as the flexible arm 106 passes over the resistance region 115 while being pushed through the inspiratory limb 104. In one embodiment, the locking comprises springing open 204 at the release region 206 until a sufficient pushing force is applied to the flexible arm 106 while being pushed in the first direction 116 through the interior flow passage 112 to activate the unlocking.

In one embodiment, the wire receiver 118 is positioned at a second end 120 of the wire adjuster 101. In one embodiment, the wire receiver 118 is configured for receiving an end portion 126 of the heating wire 102 and moving the heating wire 102 a distance in response to being pushed in the first direction 116.

Figure 6:
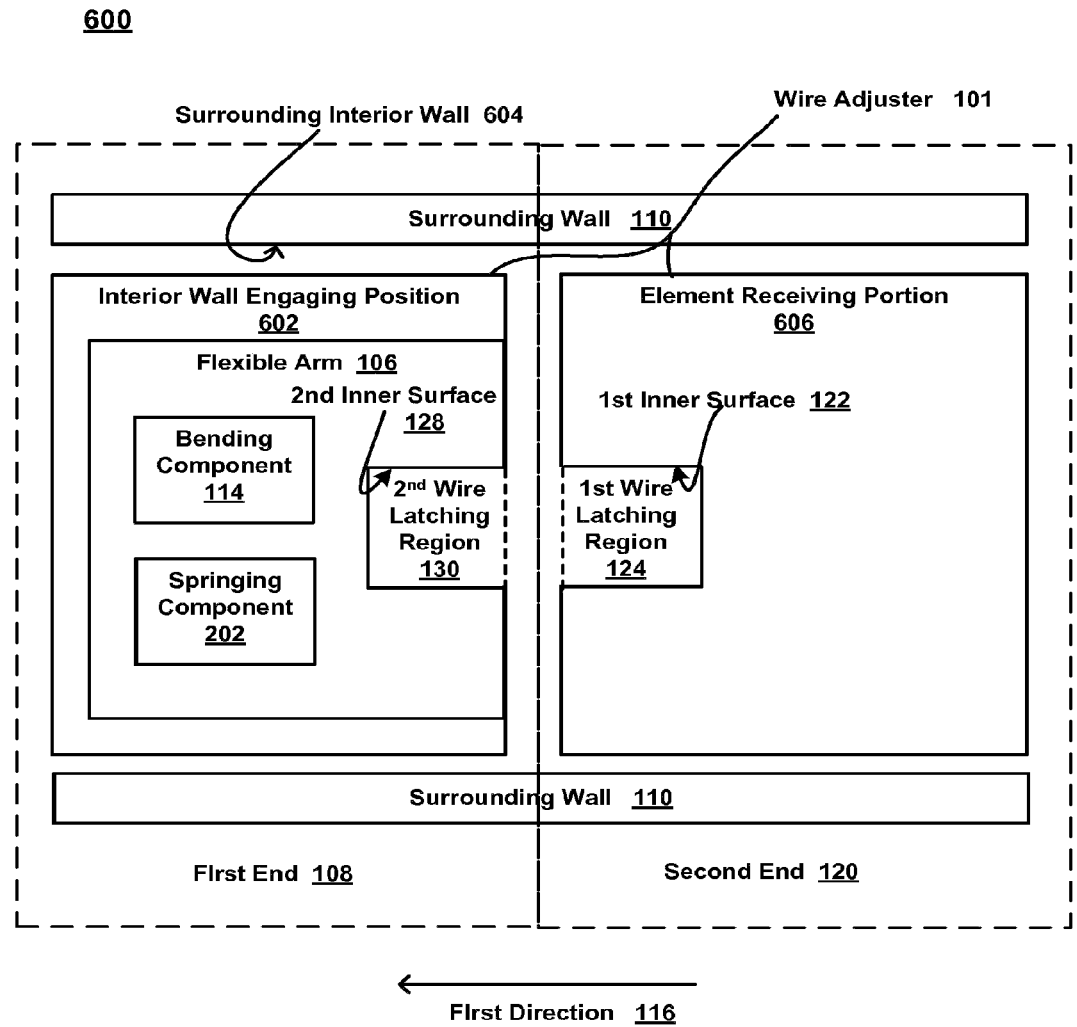
FIG. 6 is a block diagram of a wire adjuster within a limb of a breathing circuit, according to one embodiment of the present technology.

FIG. 6 is a block diagram of a wire adjuster 101 within a limb 104 of a breathing circuit, according to one embodiment of the present technology. Referring now to FIGS. 1, 2 and 6, in one embodiment, a wire adjuster 101 for adjusting a position of an element within a limb 104 of a breathing circuit comprises an interior wall engaging portion 602 coupled with an element receiving portion 606. The interior wall engaging portion 602 is configured for engaging a surrounding interior wall 604 of the limb 104. In one embodiment, the element receiving portion 606 is configured for releasably securing the element as the wire adjuster 101 is movably engaging with the surrounding interior wall 604, such that the wire adjuster 101 can be used to selectively locate an element within the limb 104 of the breathing circuit. In one embodiment, the element is a heating wire 102. In one embodiment, the interior wall engaging portion 602 comprises a flexible arm 106 positioned at the first end 108 of the wire adjuster 101, the flexible arm 106 configured for engaging a surrounding interior wall 604 of the limb 104.

Referring still to FIGS. 1, 2 and 6, in one embodiment, the element receiving portion 606 comprises a first inner surface 122 defining a first wire latching region 124, as described herein. Whereas, and as described herein, the flexible arm 106 comprises a bending component 114, a spring component 202 and a second inner surface 128 defining a second wire latching region 130.

Thus, embodiments of the present technology provide for a single breathing circuit to deliver air, anesthetics, etc. to a patient, regardless of the airflow rate that is required. The present embodiments of the breathing circuit significantly reduce hospital costs associated with storing a variety of breathing circuits for patient use.

Operation

Figure 5:
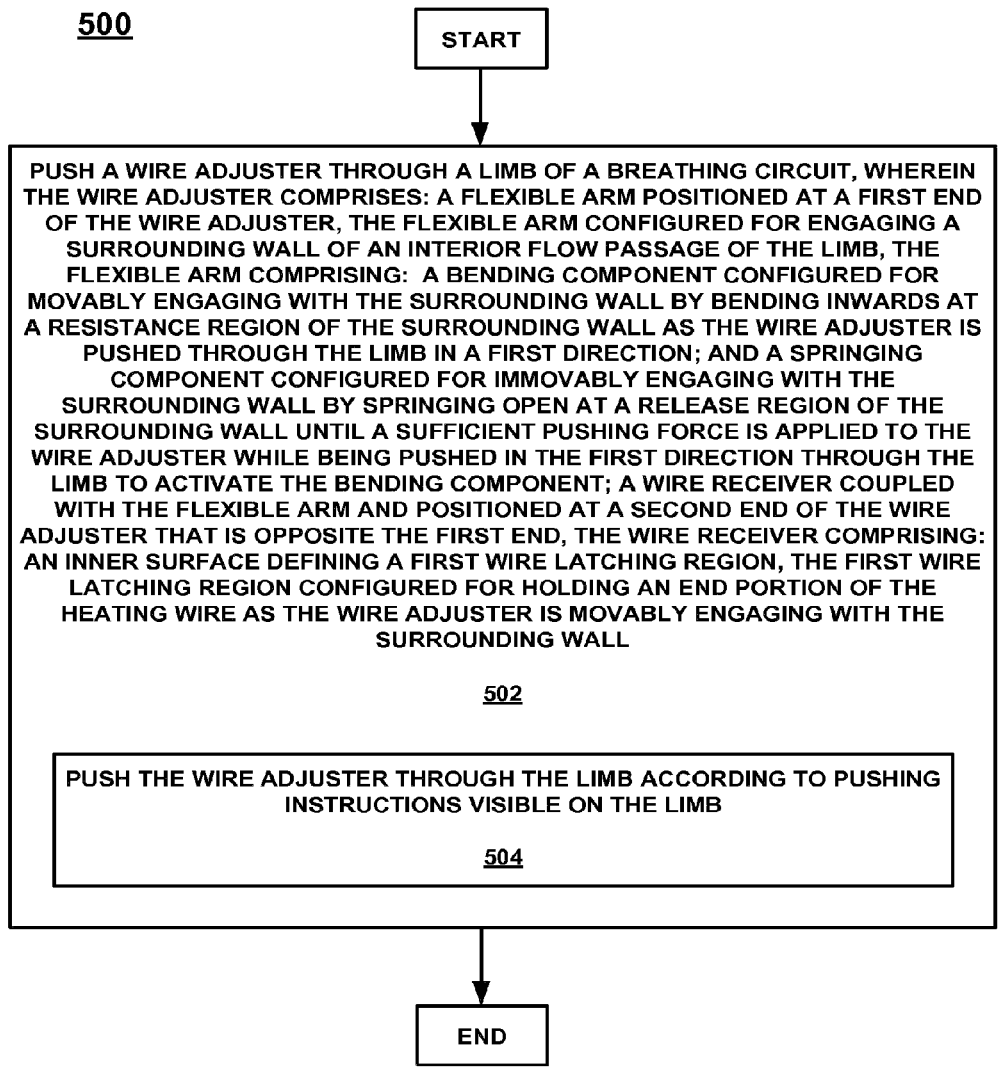
FIG. 5 is a flow diagram of a method for adjusting a position of a heating wire within a limb of a breathing circuit, according to one embodiment of the present technology.

FIG. 5 is a flow diagram of a method for adjusting a position of a heating wire 102 within a limb 104 of a breathing circuit, according to one embodiment of the present technology. Referring now to FIGS. 1, 2, 3 and 5, at 502, a wire adjuster 101 is pushed through a limb 104 of a breathing circuit. In one embodiment and as described herein, the wire adjuster 101 is pushed via a pushing device 304 similar to that outlined in FIG. 3. In one embodiment and as described herein, the wire adjuster 101 comprises a flexible arm 106 coupled with a wire receiver 118.

In one embodiment and as described herein, the flexible arm 106 comprises a bending component 114 and a springing component 202. In one embodiment and as described herein, the wire receiver 118 comprises a first inner surface 122 defining a first wire latching region 124.

At 504, the wire adjuster 101 is pushed through the limb 104 according to pushing instructions visible on the limb 104. These pushing instructions 104 may be a color code, written instructions, and any number of indications that inform/teach the user how far to push the wire adjuster 101 through the interior flow passage 112.

All statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present technology is embodied by the appended claims.

The invention claimed is:

1. A breathing circuit heating wire adjuster, comprising:
a limb of a breathing circuit;
a heating wire at least partially disposed within the limb of the breathing circuit; and
a wire adjuster, the wire adjuster comprising:
a body;
a flexible arm positioned at a first end of the body, the flexible arm configured to engage a surrounding wall of an interior flow passage of a breathing circuit limb, the flexible arm comprising:
a bending component configured to bend inwards at a resistance region of the surrounding wall as the breathing circuit heating wire adjuster is pushed through the breathing circuit limb in a first direction, the bending component configured to movably engage with the surrounding wall; and
a springing component configured to spring open at a release region of the surrounding wall, the springing component configured to engage the surrounding wall until a sufficient pushing force is applied to the breathing circuit heating wire adjuster in the first direction to activate the bending component; and
a wire receiver coupled with the flexible arm and positioned at a second end of the body opposite the first end of the body, the wire receiver comprising:
a first wire holding surface configured to hold an end portion of the heating wire; and
a second wire holding surface configured to hold the end portion of the heating wire when there is sufficient tension on the heating wire, wherein when the end portion of the heating wire is held by the second wire holding surface, the end portion of the heating wire is not in contact with the first wire holding surface.

2. The breathing circuit heating wire adjuster of claim 1, wherein the wire receiver is configured to hold a looped end portion of the heating wire.

3. The breathing circuit heating wire adjuster of claim 1, wherein the wire receiver is configured to hold a hook-shaped portion of the heating wire.

4. The breathing circuit heating wire adjuster of claim 1, the wire receiver further comprising an outer edge configured to be pushed upon by a pushing surface of a pushing device with a force that moves the breathing circuit heating wire adjuster through the interior flow passage.

5. The breathing circuit heating wire adjuster of claim 4, wherein the outer edge is flat.

6. The breathing circuit heating wire adjuster of claim 4, wherein the outer edge has a grooved surface that is compatible with the pushing surface of the pushing device.

7. The breathing circuit heating wire adjuster of claim 1, wherein an end portion of the flexible arm is configured to engage with an inner surface of a trough on a corrugated portion of the surrounding wall.

8. The breathing circuit heating wire adjuster of claim 1, wherein an end portion of the flexible arm is configured to engage with a projection on the surrounding wall.

9. The breathing circuit heating wire adjuster of claim 8, wherein the flexible arm has a pre-activation diameter, measured from a center line of the breathing circuit heating wire adjuster to the outer most points of the flexible arm, which is greater than a diameter of the wire receiver.

10. A device for movably securing a heating wire within an inspiratory limb, the device comprising:
a limb of a breathing circuit;
a heating wire at least partially disposed within the limb of the breathing circuit; and
a wire adjuster, the wire adjuster comprising:
a body;
a flexible arm positioned at a first end of the body, the flexible arm configured to:
unlock by bending inwards in response to contact with a resistance region on a surrounding wall of an interior flow passage of the inspiratory limb as the flexible arm passes over the resistance region while being pushed through the inspiratory limb; and
lock by springing open in response to contact with a release region on the surrounding wall of the interior flow passage of the inspiratory limb;
wherein a sufficient pushing force applied to the flexible arm while being pushed in the first direction through the inspiratory limb activates the unlocking;
a wire receiver coupled with the flexible arm and positioned at a second end of the body, the wire receiver comprising:
a first wire holding surface configured to hold an end portion of the heating wire; and
a second wire holding surface configured to hold the end portion of the heating wire when there is sufficient tension on the heating wire, wherein when the end portion of the heating wire is held by the second wire holding surface, the end portion of the heating wire is not in contact with the first wire holding surface.

11. The device of claim 10, wherein the wire receiver is configured to hold a looped end portion of the heating wire.

12. The device of claim 10, the wire receiver further comprising an outer edge configured to be pushed upon by a pushing surface of a pushing device with a force that moves the device through the interior flow passage.

13. The device of claim 10, wherein an end portion of the flexible arm is configured to engage with a projection on the surrounding wall.

14. The device of claim 10, wherein the flexible arm has a pre-activation diameter, measured from a center line of the breathing circuit heating wire adjuster to the outer most points of the flexible arm, which is greater than a diameter of the wire receiver.

15. An element adjustment assembly for adjusting a position of an element within a limb of a breathing circuit, the element adjustment assembly comprising:
a limb of a breathing circuit;
an element at least partially disposed within the limb of the breathing circuit; and
an element adjuster, the element adjuster comprising:
an interior wall engaging portion configured to engage a surrounding interior wall of the limb; and
an element receiving portion coupled with the interior wall engaging portion, the element receiving portion comprising:
a first element holding surface configured to hold an end portion of the element; and
a second element holding surface configured to hold the end portion of the element when there is sufficient tension on the element, wherein when the end portion of the element is held by the second element holding surface, the end portion of the element is not in contact with the first element holding surface,
wherein the element receiving portion is configured to releasably secure the element as the element adjuster is movably engaging with the surrounding interior wall, wherein the element adjuster is configured to selectively locate the element within the limb of the breathing circuit.

16. The element adjuster of claim 15, wherein the interior wall engaging portion comprises a flexible arm positioned at a first end of the element adjuster, the flexible arm configured to engage the surrounding interior wall.

17. The element adjuster of claim 16, wherein the flexible arm comprises:
- a bending component configured to movably engage with the surrounding interior wall by bending inwards at a resistance region of the surrounding interior wall as the element adjuster is pushed through the limb in a first direction; and
- a springing component configured to engage with the surrounding interior wall by springing open at a release region of the surrounding interior wall, wherein the flexible are is configured to activate the bending component when a sufficient pushing force is applied to the element adjuster while being pushed in the first direction.

18. The element adjuster of claim 15, wherein the first element holding surface defines a first element latching region, the first element latching region configured to hold the end portion of the element as the element adjuster is movably engaging with the surrounding interior wall.

19. The element adjuster of claim 15, wherein the second element holding surface defines a second element latching region that is open to the first element latching region, the second element latching region configured to hold the element when the springing component engages with the surrounding interior wall.

20. The element adjuster of claim 15, wherein the end portion of the element comprises a loop and the element receiving portion comprises a slot configured to allow the loop to pass through the slot into the element receiving portion.

* * * * *